(12) United States Patent
Satoh et al.

(10) Patent No.: US 7,361,462 B2
(45) Date of Patent: Apr. 22, 2008

(54) METHOD FOR EFFICIENTLY DETERMINING A DNA STRAND BREAK

(75) Inventors: Katsuya Satoh, Gunma (JP); Seiichi Wada, Gunma (JP); Issay Narumi, Gunma (JP); Masahiro Kikuchi, Gunma (JP); Tomoo Funayama, Gunma (JP); Yasuhiko Kobayashi, Gunma (JP)

(73) Assignee: Japan Atomic Energy Research Institute, Kashiwa (JP)

( * ) Notice: Subject to any disclaimer, the term of this patent is extended or adjusted under 35 U.S.C. 154(b) by 427 days.

(21) Appl. No.: 10/664,044

(22) Filed: Sep. 17, 2003

(65) Prior Publication Data

US 2004/0224320 A1 Nov. 11, 2004

(30) Foreign Application Priority Data

Feb. 3, 2003 (JP) ............................. 2003-026303

(51) Int. Cl.
*C12Q 1/68* (2006.01)
*G01N 33/573* (2006.01)

(52) U.S. Cl. ............................. 435/6; 435/7.1; 435/7.2; 435/7.21; 435/7.4; 435/40.5; 435/810; 435/960; 435/975

(58) Field of Classification Search .................. 435/6, 435/7.1–7.21, 7.4, 40.5–40.52, 810, 960, 435/975
See application file for complete search history.

(56) References Cited

U.S. PATENT DOCUMENTS 6,309,838 B1 * 10/2001 Chaubron et al. ............. 435/6
2003/0143707 A1 * 7/2003 Narumi et al. .............. 435/183

FOREIGN PATENT DOCUMENTS

JP 2003052376 A * 2/2003

OTHER PUBLICATIONS

Derwent Accession No. 2003-508770.*
Ngo et al, "Computational Complexity, Protein Structure Prediction, and the Levinthal Paradox", in Merz, Jr. et al (Eds.), The Protein Folding Problem and Tertiary Structure Prediction, Birkhauser, Boston, 1994, pp. 433 and 492-495.*
S. Peterson et al, Nature, 414(6):660-665, Dec. 2001.
C. L. Limoli et al, Proc. Natl. Acad. Sci. USA, 99(1):233-238, Jan. 8, 2002.

* cited by examiner

Primary Examiner—David A. Saunders

(57) ABSTRACT

The present invention is directed to directly measure distribution in vivo and the frequency of generation in vivo of DNA strand breaks which induce cell death and mutations. The present inventors accomplished the present invention by providing a method for detecting a DNA strand break in a sample, which comprises a step of binding a PprA protein derived from *Deinococcus radiodurans* to a DNA strand break and a step of detecting the PprA protein which is bound to the DNA strand break; as well as by providing a kit for detecting a DNA strand break in a sample which comprises PprA proteins derived from *Deinococcus radiodurans* and a means for detecting a PprA protein which is bound to a DNA strand break.

4 Claims, 6 Drawing Sheets

SEQUENCE LISTING

```
<160> NUMBER OF SEQ ID NOS: 4

<210> SEQ ID NO 1
<211> LENGTH: 284
<212> TYPE: PRT
<213> ORGANISM: Deinococcus radiodurans, strain KD8301
<220> FEATURE:
<223> OTHER INFORMATION: Amino acid sequence of DNA repair promoting
      protein, PprA, of Deinococcus radiodurans, strain KD8301.

<400> SEQUENCE: 1

Met Ala Arg Ala Lys Ala Lys Asp Gln Thr Asp Gly Ile Tyr Ala Ala
1               5                   10                  15

Phe Asp Thr Leu Met Ser Thr Ala Gly Val Asp Ser Gln Ile Ala Ala
            20                  25                  30

Leu Ala Ala Ser Glu Ala Asp Ala Gly Thr Leu Asp Ala Ala Leu Thr
        35                  40                  45

Gln Ser Leu Gln Glu Ala Gln Gly Arg Trp Gly Leu Gly Leu His His
    50                  55                  60

Leu Arg His Glu Ala Arg Leu Thr Asp Asp Gly Asp Ile Glu Ile Leu
65                  70                  75                  80

Thr Asp Gly Arg Pro Ser Ala Arg Val Ser Glu Gly Phe Gly Ala Leu
                85                  90                  95

Ala Gln Ala Tyr Ala Pro Met Gln Ala Leu Asp Glu Arg Gly Leu Ser
            100                 105                 110

Gln Trp Ala Ala Leu Gly Glu Gly Tyr Arg Ala Pro Gly Asp Leu Pro
        115                 120                 125

Leu Ala Gln Leu Lys Val Leu Ile Glu His Ala Arg Asp Phe Glu Thr
    130                 135                 140

Asp Trp Ser Ala Gly Arg Gly Glu Thr Phe Gln Arg Val Trp Arg Lys
145                 150                 155                 160

Gly Asp Thr Leu Phe Val Glu Val Ala Arg Pro Ala Ser Ala Glu Ala
                165                 170                 175

Ala Leu Ser Asp Ala Ala Trp Asp Val Ile Ala Ser Ile Lys Asp Arg
            180                 185                 190

Ala Phe Gln Arg Glu Leu Met Arg Arg Ser Glu Lys Asp Gly Met Leu
        195                 200                 205

Gly Ala Leu Leu Gly Ala Arg His Ala Gly Ala Lys Ala Asn Leu Ala
    210                 215                 220

Gln Leu Pro Glu Ala His Phe Thr Val Gln Ala Phe Val Gln Thr Leu
225                 230                 235                 240

Ser Gly Ala Ala Ala Arg Asn Ala Glu Glu Tyr Arg Ala Ala Leu Lys
                245                 250                 255
```

```
Thr Ala Ala Ala Ala Leu Glu Glu Tyr Gln Gly Val Thr Thr Arg Gln
        260                 265                 270

Leu Ser Glu Val Leu Arg His Gly Leu Arg Glu Ser
    275                 280
```

<210> SEQ ID NO 2
<211> LENGTH: 855
<212> TYPE: DNA
<213> ORGANISM: Deinococcus radiodurans, strain KD8301
<220> FEATURE:
<223> OTHER INFORMATION: Nucleotide sequence of DNA repair promoting
      protein, pprA, of Deinococcus radiodurans, strain KD8301.

<400> SEQUENCE: 2

| | | |
|---|---|---|
| atggcaaggg ctaaagcaaa agaccaaacg gacggcatct acgccgcctt cgacaccttg | 60 |
| atgagcacgg cgggcgtgga cagccagatc gccgccctcg ccgcgagtga ggccgacgcg | 120 |
| ggcacgctgg acgcggcgct cacgcagtcc ttgcaagaag cgcaggggcg ctggggctg  | 180 |
| gggctgcacc acctgcgcca tgaggcgcgg ctgaccgacg acggcgacat cgaaattctg | 240 |
| accgatggcc gccccagcgc ccgcgtgagc gagggcttcg gagcactcgc gcaggcctac | 300 |
| gcgcccatgc aggcgctcga cgaacgcggc ctgagccagt gggcggcgct cggcgagggc | 360 |
| taccgcgctc ccggcgactt gccgttggcg cagctcaagg tgctgatcga gcacgcccgc | 420 |
| gacttcgaaa ccgactggtc ggcggggcgc ggcgaaacct ttcagcgcgt gtggcgcaag | 480 |
| ggcgacaccc tgtttgtcga ggtggcccgg cccgcgtccg ccgaggccgc gctctccgac | 540 |
| gctgcctggg acgtgatcgc cagcatcaag gaccgcgcct tccagcgtga gctgatgcgc | 600 |
| cgcagcgaga aggacgggat gctcggcgcc ctgctcgggg ctcgccacgc cggggccaag | 660 |
| gccaacctcg cccagctgcc cgaagcgcac ttcaccgtgc aggcgttcgt gcagaccctc | 720 |
| agcggagccg ccgccgcaa cgccgaggag taccgcgcgg ccctgaaaac cgccgccgct | 780 |
| gcgctggagg aataccaggg cgtgaccacc cgccaactgt ccgaagtgct gcggcacggc | 840 |
| ctgcgcgaga gctga | 855 |

<210> SEQ ID NO 3
<211> LENGTH: 35
<212> TYPE: DNA
<213> ORGANISM: Deinococcus radiodurans
<220> FEATURE:
<223> OTHER INFORMATION: Sense primer for amplifying pprA gene.

<400> SEQUENCE: 3
gggcataata aaggccatat ggcaagggct aaagc                                35

<210> SEQ ID NO 4
<211> LENGTH: 32
<212> TYPE: DNA
<213> ORGANISM: Deinococcus radiodurans
<220> FEATURE:
<223> OTHER INFORMATION: Antisense primer for amplifying pprA gene.

<400> SEQUENCE: 4
ttttggatcc tcagctctcg cgcaggccgt gc                                   32

US 7,361,462 B2

METHOD FOR EFFICIENTLY DETERMINING A DNA STRAND BREAK

BACKGROUND OF THE INVENTION

This application is based upon and claims the benefit of priority from Japanese Patent Application No. 2003-26303, filed on Feb. 3, 2003; the entire contents of this application are incorporated herein by reference.

The present invention is directed to a method for detecting a DNA strand break using a PprA protein derived from *Deinococcus radiodurans* which recognizes and binds to a DNA strand break. The present invention is also directed to a kit for detecting one or more DNA strand break which comprises an amount of PprA protein derived from *Deinococcus radiodurans* which recognize and bind to one or more DNA strand break.

It is essential for continued existence of species that DNA, a carrier of genetic information, be stably maintained, and transferred to progeny. However, living organisms are continually exposed to environmental factors which trigger damage to DNA. Such factors consist of extrinsic such as radiation, ultraviolet rays, agents, or other mutagens which are present in foods and in the environment in general, and of intrinsic factors such as active oxygen, which is generated in the process of metabolism, and also error(s) in DNA replication. Such DNA damage inhibits the replication or transcription of DNA, resulting in mutation which may cause cell death, aging, tumorigenesis or carcinogenesis.

A DNA strand break is a particularly serious form of DNA damage and has an especially deleterious effect on cells. Therefore, from the viewpoint of risk assessment, it is believed to be important to examine a frequency of generation of DNA strand break(s), a distribution of DNA strand break(s) in cells, and differences in susceptibility between DNA strand break(s) and other DNA damage. However, to date there has existed no known sufficiently sensitive method for directly detecting a life-threatening DNA strand break. This was resulted in a delay in technical progress in the art. Therefore, it is important for technical progress in the field relating to DNA damage and DNA repair of higher organisms to be able to directly examine a distribution of and repair process of DNA strand break(s), through the development of an in situ method of visualizing DNA damage and DNA repair.

To date, several examples are known for detecting DNA strand break(s) using DNA binding protein and antibodies which specifically bind thereto in mammalian cells such as follows: one example it to use, in B lymphocytes, Nbs1 protein, Rad51 protein, Brca1 protein, or gamma-H2AX protein, and antibodies which specifically bind to these proteins to detect DNA strand break(s) (Petersen et al., Nature, 414: 660-665, 2001); and another example is to use, in human fibroblast cells, Mre11 protein or gamma-H2AX protein and antibodies which specifically bind to these proteins to detect DNA strand break(s) (Limoli et al., Proc. Natl. Acad. Sci. USA, 99: 233-238, 2002).

However, since endogenous DNA binding proteins are used in these methods for detecting DNA strand break(s), these methods have disadvantages that DNA strand break(s) cannot be detected in a sample which is prepared from an organism not having such DNA binding proteins, and that it is difficult to detect initial damage of DNA because it takes a certain period to bind DNA binding protein to DNA strand break(s).

The present invention is directed to a method for directly measuring the in vivo distribution and the frequency of generation of DNA strand break(s) which triggers cell death and mutation. More specifically, the present invention is directed to a method for detecting a DNA strand break using a Ppra protein derived from *Deinococcus radiodurans* which has an ability to recognize and bind to a DNA strand break, well as a kit for detecting a DNA strand break comprising an amount of Ppra protein.

SUMMARY OF THE INVENTION

In view of the problems existing in the prior art, the present inventors conducted extensive studies with the aim of developing a method for detecting a DNA strand break using a protein which has a potent and specific binding activity to the DNA strand break. As a result, the present inventors determined that it is possible to specifically and sensitively detect DNA strand break(s) in a sample by binding a Ppra protein derived from *Deinococcus radiodurans* to a DNA strand break and by detecting the Ppra protein bound to the DNA strand break and, as a result, completed the present invention.

Thus, the present invention solves the problems of the prior art described above by providing a method for detecting a DNA strand break in a sample by binding a PprA protein derived from *Deinococcus radiodurans* or a fragment thereof to a DNA strand break and detecting the PprA protein or a fragment thereof bound to the DNA strand break.

The present invention also solves the problems of the prior art described above by providing a kit for detecting a DNA strand break in a sample comprising an amount of PprA protein derived from *Deinococcus radiodurans* or a fragment thereof, and a means for detecting the PprA protein or a fragment thereof.

Figure 1:
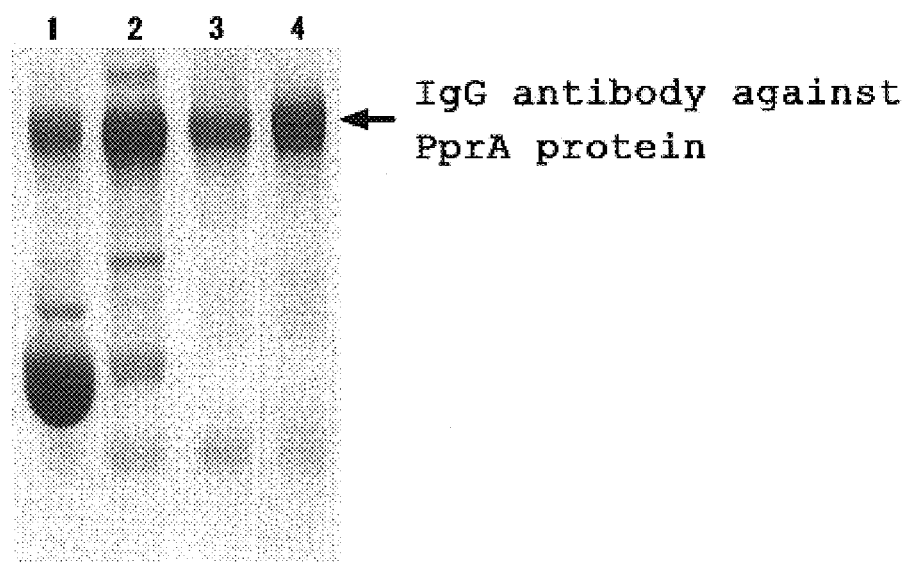
FIG. 1 is a photograph showing Coomassie staining of SDS-PAGE electrophoresis about IgG antibodies in various purification steps.

an image of DNA strand breaks detected by fluorescence of Cy2 after 10 Gy of gamma ray irradiation; and (D) an image of DNA strand breaks detected by fluorescence of Cy2 after 20 Gy of gamma ray irradiation.

DETAILED DESCRIPTION OF THE INVENTION

In one embodiment, the present invention provides a method which can detect a DNA strand break in a sample, wherein the method comprises a step of binding of a PprA protein derived from *Deinococcus radiodurans* or a fragment thereof to a DNA strand break and a step of detecting the PprA protein or a fragment thereof bound to the DNA strand break.

The present inventors previously found a novel protein, PprA, having a DNA repair promoting activity from radiation resistant bacterium, *Deinococcus radiodurans*; and also found that this protein specifically recognizes and binds to an open circular double-stranded DNA with nicks and a linear double-stranded DNA (Japanese Patent Public Disclosure (JP-A) No. 052376/2003; corresponding to Japanese patent application No. 246260/2001).

In the present invention, first of all, a DNA strand break in cells is recognized by use of a PprA protein. More specifically, the PprA protein derived from *Deinococcus radiodurans* or a fragment thereof which has an activity to bind to a DNA strand break is attached to the DNA strand break in a sample, such as a DNA sample from a nucleus of a cell or a DNA sample from other intracellular organelles (such as mitochondria).

In examining a DNA strand break in culture cells, after cells which are cultured on a cover glass are fixed in a fixation solution, the binding of a PprA protein or a fragment thereof to an intracellular DNA strand break can be examined in situ in culture cells by incubation in a solution containing PprA proteins or a fragment thereof. In examining a DNA strand break in tissue cells, a paraffin embedded tissue section is deparaffinized and rehydrated, which is followed by examining the binding of a PprA protein or a fragment thereof to an intracellular DNA strand break in situ in tissue cells by incubating the tissue section in a solution containing PprA proteins or a fragment thereof.

In the present invention, the term "a DNA strand break" means one or more instances of DNA damage in which at least a portion of sugar-phosphate linkages consisting of DNA (backbone) is disrupted or cleaved. The term "a DNA strand break" includes a case in which only a single-strand out of two backbones of a duplex is cleaved (single-strand breaks), and a case in which both strands of DNA duplex are cleaved (double-strand breaks). Such a DNA strand break is caused by extrinsic factors such as ionizing radiation, ultraviolet rays, agents, or other mutagens which are present in food or environment, or intrinsic factors such as an active oxygen, which is generated in the process of metabolism, and error(s) upon DNA replication.

In the context of the present invention, a protein which has an ability to recognize and bind a DNA strand break (PprA) means a protein which does not bind to an intact DNA but specifically binds to DNA single strand break(s) or DNA double strand break(s). Further, the term "a fragment" of a PprA protein means one or more fragments of the PprA protein which does not bind to an intact DNA but specifically binds to a DNA single strand break or a DNA double strand break. It is preferred that the PprA protein having such characteristics as described above is, for example, a protein having an amino acid sequence as depicted in SEQ ID NO: 1. It is also preferred that a fragment of the PprA protein is a fragment having a portion of an amino acid sequence of SEQ ID NO: 1 and having an ability to recognize and bind to a DNA strand break.

The PprA protein or a fragment thereof having an ability to recognize and bind to a DNA strand break can be prepared according to the methods which are known in the art, for example, typically, the methods described in the following publications: Simon (Protein Purification Techniques: A Practical Approach, The Practical Approach Series, 244, 2nd edition (2001)); Simon (Protein Purification Applications: A Practical Approach, The Practical Approach Series, 245, 2nd edition (2001)); Hardin (Cloning, Gene Expression and Protein Purification: Experimental Procedures and Process Rationale (2001)). More specifically, the PprA protein or a fragment thereof having an ability to recognize and bind to a DNA strand break can be prepared according to the method described in Japanese Patent Public Diclosure No. 2003-052376 (JP-A-052376/2003, corresponding to Japanese patent application No. 246260/2001).

Briefly, the PprA protein (SEQ ID NO: 1) can be prepared by the following method: A pair of primers (for example, SEQ ID NO: 3 and SEQ ID NO: 4) is used in PCR method to amplify a nucleotide sequence (SEQ ID NO: 2) encoding the PprA protein, which is inserted into a commercially available vector such as pUC19 (Takara Shuzo), pBluescript II KS(+) (Stratagene), pET3a (Novagen) to make recombinant vectors; then the recombinant vectors are introduced into host cells such as *E. coli, Bacillus subtilis*, yeast and mammalian cells using known transforming methods as described in detail in Sambrook and Russel (Molecular Cloning: A Laboratory Manual, 3rd edition (2001)); Hardin (Cloning, Gene Expression and Protein Purification: Experimental Procedures and Process Rationale (2001)); Brown (Essential Molecular Biology: A Practical Approach, Vol. 1, 2nd edition (2001)) to generate transformants; after which, these transformants can be cultured under the appropriate conditions to produce the PprA protein (SEQ ID NO: 1) and to grow these host cells. Finally, the PprA protein which is produced in the cells can be prepared by the steps of disrupting the harvested transformants using ultrasonication, of removing the thus produced PprA protein in a supernatant by centrifugation, and of purifying the desired protein from the supernatant by column chromatography using such as a commercially available ion-exchange resin, a gel-filtration carrier, an affinity resin, and so on.

Further, in the present invention, it is possible to use a fragment of the PprA protein having an ability to specifically recognize and bind to a DNA strand break. Such a fragment may be obtainable by a genetically-engineered method as described above in which a nucleotide sequence encoding a fragment of the desired protein is expressed, or by a proteinase digestion of the PprA protein using a known method such as a method of digesting the protein by trypsin or pepsin.

Then, in the method of the present invention, the PprA protein or a fragment thereof which binds to a DNA strand break is detected. The PprA protein or a fragment thereof may be detected using a molecule which specifically binds to the PprA protein or a fragment thereof, such as an antibody or a fragment thereof which specifically binds to the PprA protein or a fragment thereof, a peptide, and so on. In the present invention, it is preferable to use an antibody or a fragment thereof which specifically binds to the PprA protein or a fragment thereof. In the context of the present invention, the term "specifically bind" means that something specifically binds to the PprA protein or a fragment thereof, but can not to cross-react with proteins other than the PprA protein or a fragment thereof.

A molecule which specifically binds to the PprA protein or a fragment thereof may be detected by binding a means for visualizing the molecule, such as a fluorescent dye, a radioisotope (such as $^{35}S$ or $^{3}H$), an enzyme (such as horseradish peroxidase), or an appropriate affinity ligand (such as avidin-biotin) labeled with a fluorescent dye, to the PprA protein or a fragment thereof; or by binding an antibody, which specifically binds these molecules with a means for visualizing an antibody as described above, to the PprA protein or a fragment thereof. In the present invention, it is preferable to use a fluorescent dye or an affinity ligand bound to a fluorescent dye from the viewpoint of sensitivity, ease of operation, and margin of safety. Various fluorescent dyes, such as Cy2, FITC, Alexa-350, and Rhodamine B, may be used to label these molecules fluorescently. These molecules may be easily labeled with the fluorescent dyes mentioned above using a commercially available kit. The use of the molecules labeled with each one of these fluorescent dyes makes it possible to visualize a DNA strand break specifically and with high sensitivity under a fluorescent microscope, so as to measure the frequency of the DNA strand breaks and to detect the small number of DNA strand breaks contained in a sample.

In the present invention, a molecule which specifically binds to the PprA protein or a fragment thereof is used to detect the PprA protein or a fragment thereof bound to a DNA strand break in accordance with the following method: first of all, a sample (such as culture cells or a tissue section) is washed completely to remove an unbound PprA protein or a fragment thereof from the sample; then, the sample is incubated with a buffer solution containing an antibody to bind the antibody to the PprA protein or a fragment thereof bound on the sample.

If an antibody is used as a molecule which specifically binds to the PprA protein or a fragment thereof, an antibody may be either a polyclonal antibody or a monoclonal antibody. A fragment of the antibody having a similar binding activity as the antibody (such as Fab, F(ab')$_2$, Fab' and so on) may also be used in the present invention. A polyclonal antibody is obtainable from an antiserum which is collected from an applicable animal such as a rabbit, a sheep, a goat, a guinea pig, or mouse which is immunized against a protein having an ability to recognize and bind to a DNA strand break (PprA) or a fragment thereof. A monoclonal antibody may be obtainable by the following method: an antibody-forming cell is collected from an animal which is immunized against a protein having an ability to recognize and bind to a DNA strand break (PprA) or a fragment thereof; the antibody-forming cell is hybridized with an applicable fusion partner cell to make a hybridoma cell; the hybridoma cell is cultured in a medium suitable for growing the cells; the cell which produces an antibody having a necessary activity is cloned; the cloned hybridoma cell is cultured under an appropriate condition; and a monoclonal antibody can obtained from the supernatant of the cloned hybridoma cell. Moreover, a monoclonal antibody may be produced by transplanting and growing thus cloned hybridoma cell intraperitoneally. It is preferable that an animal used as one suitable for immunization be a mouse, a nude mouse, a rat or a chicken. An antibody may be purified by a common isolation and purification method in the art such as centrifugation, dialysis, ammonium sulfate salting-out, ion-exchange chromatography, gel filtration, affinity chromatography, and so on.

A means for visualization can be effected by any suitable method known in the art. For example, when a fluorescent dye is used as a means for visualization, a fluorescence from the fluorescent dye can be visualized by irradiating a laser beam having the specific excitation wavelength for the fluorescent dye to a sample and observing an emission light emitted from the fluorescent dye having a specific wavelength using a fluorescent microscope and/or a CCD camera. When a radioisotope is used as a means for visualization, radiation can be visualized using a means such as a scintillation counter, an exposure of the radiation on an X ray film, an exposure of the radiation on an imaging plate, and so on. When an enzyme is used as a means for visualization, a faint light developed from a color development kit by the action of the enzyme can be detected by the exposure of the faint light on an X ray film.

In another embodiment, the present invention provides a kit for detecting a DNA strand break in a sample comprising an amount of PprA protein derived from *Deinococcus radiodurans* or a fragment thereof and a means for detecting the PprA protein or a fragment thereof. A means for detecting the PprA protein or a fragment thereof includes a fluorescence labeled antibody or a fragment thereof which specifically binds to the PprA protein or a fragment thereof.

Further, the kit of the present invention may include an instruction for use which illustrates a step of binding a PprA protein or a fragment thereof to a DNA strand break in a sample and a step of detecting the PprA protein or a fragment thereof bound to the DNA strand break in a sample using a means for detection. Further, the kit of the present invention may include one or more additional agents such as buffer as used in the present invention.

EXAMPLE

The present inventors describe Examples hereinafter. However, the following Examples are described only for illustrating the present invention more specifically. Therefore, the descriptions of these Example are not intended to limit the extent of the present invention.

Example 1

Production of a Polyclonal Antibody which Recognize a Protein Having an Ability to Recognize and Bind to DNA Strand Break (PprA)

(1) Preparation of the PprA Protein

The protein, PprA, was prepared according to the method described in Japanese Patent Public Diclosure No. 2003-052376 (JP-A-052376/2003, corresponding to Japanese patent application No. 246260/2001). More specifically, the protein, PprA, was prepared by the method below:

PCR was carried out using a full-length pprA gene encoding the PprA protein which was contained in a plasmid as a template and primers (primer 1: 5'-gggcataata aaggccatat ggcaagggct aaagc-3' (SEQ ID NO: 3) and primer 2: 5'-ttttggatcc tcagctctcg cgcaggccgt gc-3' (SEQ ID NO: 4)) to amplify the gene pprA having 855 bp of an open reading frame (SEQ ID NO: 2). The pprA gene was integrated into *E. coli* expression vector pET3a (Novagen) to prepare an expression vector called pET3pprAwt.

Then, the pET3pprAwt plasmid as prepared above was used to transform *E. coli* BL21 (DE3) pLysS (Novagen). Each transformants were separately cultured in LB medium (BD Bioscience) containing ampicillin and chloramphenicol. At the time when the optical densities at wave length of 600 nm reached to O.D. 0.6, a final concentration of 0.4 mM of IPTG (isopropyl-β-D-thiogalactopyranoside, Takara Shuzo) was added to the culture medium to induce the protein production.

After additionally culturing *E. coli* transformants for 3 hours, the culture media were centrifuged to form pellets of the transformants. Each of the pellets of the transformants was suspended in a bacteriolysis buffer (20 mM Tris-HCl, pH 8.0, 2 mM EDTA, 1 mM PMSF), which were subjected to ultrasonication. After that, the ultrasonicated suspensions were centrifuged at 8,000 rpm for 30 minutes. Supernatants were collected from each centrifuged samples and crudely purified proteins were prepared.

The crudely purified proteins were purified using polyamine treatment method, ammonium sulfate salting-out method, DEAE sepharose CL-6B column chromatography method (Amersham Pharmacia Biotech), sephacryl S-300 gel filtration method (Amersham Pharmacia Biotech), and mono Q column chromatography method (Amersham Pharmacia Biotech) to prepare the purified wild-type PprA protein.

(2) Preparation of a Fluorescence Labeled Polyclonal Antibody

A rabbit was subcutaneously immunized against the purified protein as prepared by the method (1) above as an immunogen in 100 μl of emulsion solution of the protein with Freund's oil-based adjuvant. The rabbit was boosted with the same amount of emulsion containing the antigen and Freund's oil-based adjuvant twice a mouth (total 6 times). Whole blood was collected one month after the last boost. An antiserum was obtained by centrifugation of the whole blood, which was heat inactivated and, then, was stored −80° C. after addition of 0.05% $NaN_3$.

The obtained antiserum was purified with ammonium sulfate salting-out method, rProtein A sepharose column chromatography method(Amersham Biosciences), and mono S column chromatography method(Amersham Biosciences). As a result, a highly pure polyclonal IgG antibody was prepared from an antiserum derived from the immunized rabbit (FIG. 1). In this figure, each lanes show the results of the followings: lane 1, an antiserum; lane 2, ammonium sulfate treatment; lane 3, rProtein A column chromatography; lane 4, mono S column chromatography.

Figure 2:
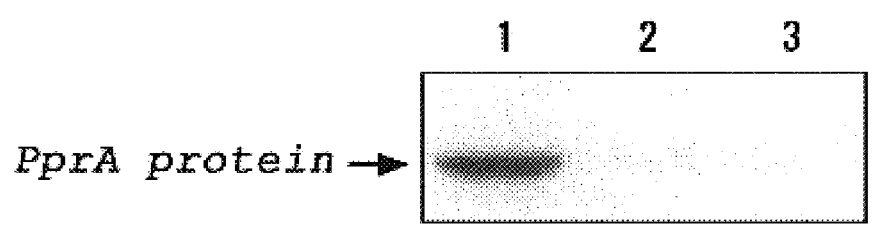
FIG. 2 is a photograph showing the results of analysis by Western Blotting of the PprA protein derived from *Deinococcus radiodurans* cells and mammalian cells (CHO-K1).

The specificity of the polyclonal IgG antibody was determined by examining whether the antibody could detect PprA which was existed within *Deinococcus radiodurans* cells and mammalian cells (CHO-K1 cells). Protein extract solutions were prepared by a step of crushing *Deinococcus radiodurans* wild-type strain, *Deinococcus radiodurans* pprA gene disrupted strain, and CHO-K1 cells using glass beads to prepare suspensions of these cells and by a step of centrifuging these suspensions. The protein extract solutions were subjected to SDS-PAGE, which was followed by transferring the proteins to the membrane filter (Millipore) to conduct the western blotting analysis using the purified antibody as prepared above. As a result, the PprA protein was detected in the wild-type strain of *Deinococcus radiodurans*, while the PprA protein could not be detected in the pprA gene-disrupted strain and CHO-K1 cells (FIG. 2). In this figure, lane 1 shows the result from the wild-type strain of *Deinococcus radiodurans*; lane 2 shows the result from the pprA gene-disrupted strain of *Deinococcus radiodurans*; and lane 3 shows the result from CHO-K1 cells. Therefore, the specificity of the polyclonal IgG antibody as prepared against the PprA protein was confirmed.

Cy2 molecules were linked through ester bond to free amino acid residues in the polyclonal IgG antibody as prepared above using Cy2 Ab Labeling Kit (Amersham Biosciences) to produce a fluorescence labeled polyclonal IgG antibody.

Example 2

A Method for Detecting a DNA Strand Break In a Mammalian Cell Nucleus Using a Protein Having an Activity to Recognize and Bind to a DNA Strand Break and an Antibody which Specifically Binds Thereto An example is shown here in which a DNA strand break induced by gamma ray irradiation within a nucleus of a fibroblast cell derived from Chinese hamster ovary (CHO-K1) could be detected using a protein having a DNA binding activity which was prepared in Example 1 and a fluorescent labeled polyclonal anti-PprA IgG antibody.

(1) Preparation of Cells

CHO-K1 cells are cultured using Ham's F12 culture medium supplemented with 10% FCS in $CO_2$ incubator (5% $CO_2$) at 37° C. After removing the culture medium from a culture dish using an aspirator, the cells which were attached to the culture dish were washed twice using the bivalent ions free-phosphate buffered saline (PBS (−)). After washing, by adding PBS (−) containing 0.05% trypsin and 0.02% EDTA to the cells, and by stirring the dish mildly, adhesions between cells-to-cells or cells-to-dish were disrupted. After then, to inactivate trypsin, an additional Ham's F12 culture medium supplemented with 10% FCS was added to the cells to prepare a single cell suspension containing $1\times10^6$ cells/ml.

A cover glass (24×24 mm) was placed in 35 mm culture dish after being sterilized by the dry-heat sterilization method. The prepared cell suspension was applied to the cover glass and were cultured in $CO_2$ incubator (5% $CO_2$) for 2 hours at 37° C. to adhere the cells on the cover glass. Then, Ham's F12 culture medium supplemented with 10% FCS was added to the culture dish and the cells were cultured in $CO_2$ incubator (5% $CO_2$) for 18 hours at 37° C., resulting in the cells which were uniformly attached onto a cover glass.

(2) Gamma Ray Irradiation

To cleave DNA of CHO-K1 cells which adhered to a cover glass, the cells were irradiated with 0, 0.5, 1, 5, 30, 50, 75, or 100 Gy of gamma ray which was generated from $^{60}Co$ as a radiation source in the culture medium. Doses of irradiation were controlled by varying distances between the radiation source and the samples.

(3) Fixation Of Cells

Just after the irradiation, the culture medium was removed by an aspirator from the culture dish, a fixation solution (10 mM Tris-HCl containing 4% paraformaldehyde and 50 mM EDTA (pH 7.6)) was added to the culture dish containing the cells and the cells were incubated with the fixation solution for 30 minutes at 4° C.

(4) Permeabilization Of Plasma Membrane

Fixed cells were washed twice with Buffer 1 (10 mM Tris-HCl (pH 7.6), 10 mM $MgCl_2$, 1 mM DTT), with mild stirring for 5 minutes at room temperature. After washing, Buffer 1 supplemented with 1 μg/ml of Protenase K and 1% SDS is added to the cells to react for 30 seconds at room temperature. After the reaction, the cells were washed three times with Buffer 1, with mild stirring, for 5 minutes at room temperature. Then, plasma membranes of the cells were permeabilized by incubating the cells with Buffer 1 supplemented with 1% Nonidet P40 (Roche) for 90 minutes at 37° C. Further, the cells were washed three times with Buffer 1 with mild stirring.

(5) Treatment using a Protein Having an Ability to Recognize and Bind to a DNA Strand Break To avoid non-specific absorbance of the PprA protein, Buffer 1 containing 1% BSA was added to the cells to block the cells for 60 minutes at 37° C. After that, a solution of the protein having an ability to recognize and bind to a DNA strand break (PprA) as prepared in Example 1-(1) at the concentration of 250 ng/ml in Buffer 2 (10 mM Tris-HCl (pH 7.6), 10 mM $MgCl_2$, 1 mM DTT, 0.1% BSA) were added to the cells, which were incubated for 60 minutes at 37° C. Then, to remove an unreacted PprA protein, the cells were washed twice with mild stirring using Buffer 2 containing 0.5% Triton X-100 for 5 minutes at room temperature.

(6) Treatment with a Fluorescence Labeled IgG Antibody

A Cy2-labeled anti-PprA IgG antibody was prepared according the same method as Example 1-(2), which is diluted in Buffer 2 to prepare a solution containing the antibody at a concentration of 2 µg/ml. The thus prepared solution was added to the cells, followed by incubation for 60 minutes at 37° C. under light shielding. Then, to remove an unbound antibody, the cells were washed twice with mild stirring using Buffer 2 containing 0.5% Triton X-100 for 5 minutes at room temperature.

(7) Microscopic Observation and Measurement of Fluorescence Intensities

After adding DAPI solution (0.1 µg/ml) to the cells adherent to the cover glass in order to stain their nuclei, a discoloration inhibitory solution (glycerol containing 0.5% p-phenylenediamine) was dropped on a slide glass, on which the cover glass was placed with care being taken to ensure that there would be no air bubbles left between the two glasses. To avoid evaporating moisture, a mounting agent was applied around the cover glass. Setting filters for the fluorescence of DAPI (excitation wavelength at 360 nm) or that of Cy2 (excitation wavelength at 489 nm), the samples were observed using a fluorescence microscope. Photographs of the produced fluorescence signal were taken by CCD camera. As a result, it was confirmed that fluorescence images of the nuclei of the cells visualized using DAPI completely corresponded to that using Cy2 and that, therefore, the present method could effectively detect a DNA strand break existed in the nuclei of the cells (FIG. 3).

Figure 3:
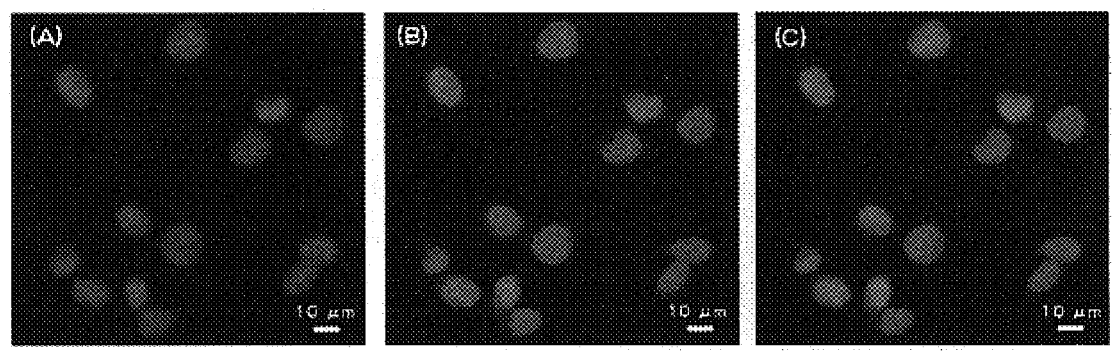
FIG. 3 consists of copies of photographs showing DNA strand breaks in CHO-K1 cells after gamma ray irradiation: (A) an image of nuclei detected by fluorescence of DAPI; (B) an image of DNA strand breaks detected by fluorescence of Cy2; and (C) an image in which the fluorescence of DAPI (A) and that of Cy2 (B) are overlaid.
Figure 4:
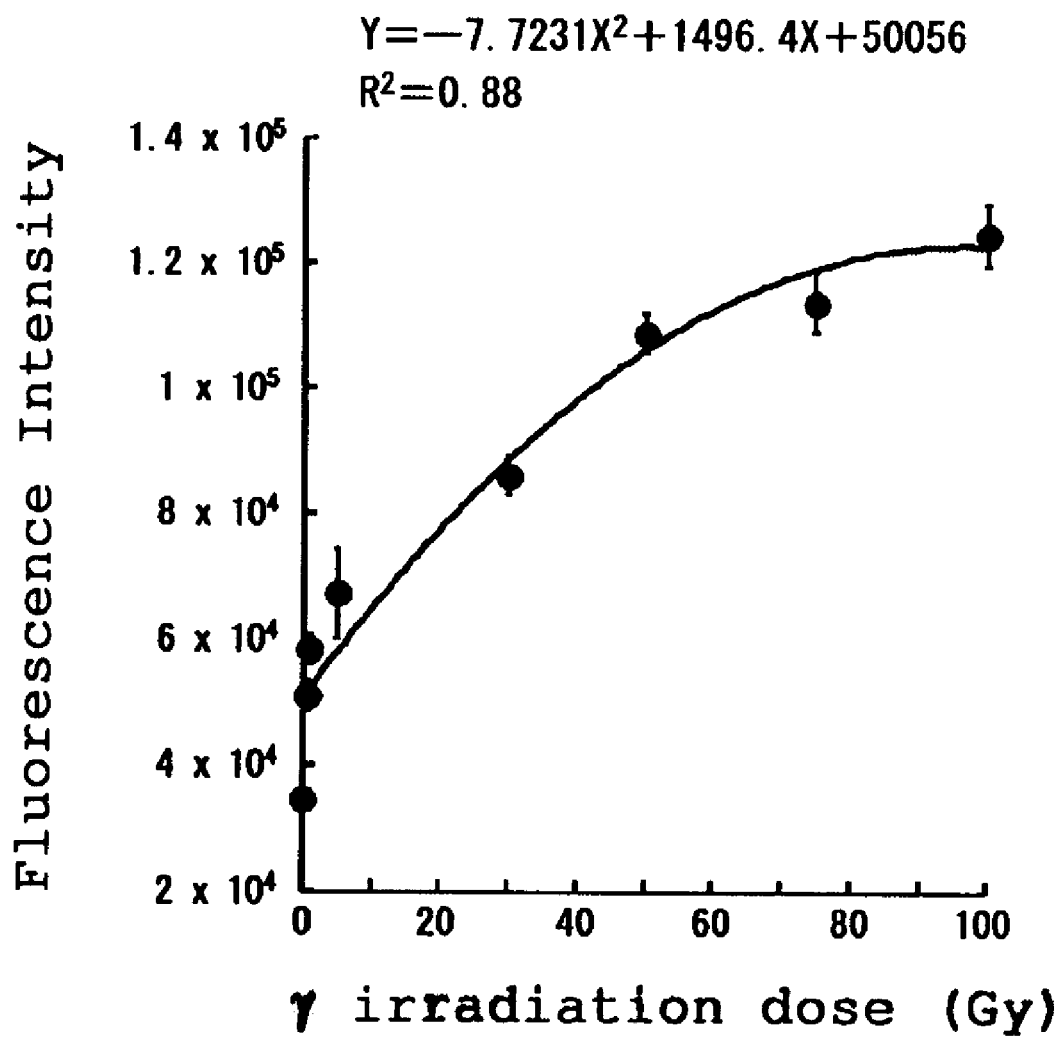
FIG. 4 is a graph showing the results of a measurement value of the fluorescence intensity of Cy2 in relation to a gamma ray dose regarding DNA strand breaks in CHO-K1 cells after gamma ray irradiation.

Based on the photographs shown in FIG. 3, fluorescence intensities of Cy2 were measured using an analysis software, Komet 4.0 (KINETIC IMAGING, LTD.). As a result, a dose dependency of the number of DNA strand breaks in CHO-K1 cells on dose of gamma ray was confirmed (FIG. 4).

Example 3

A Method for Detecting a DNA Strand Break in Mitochondria of Mammalian Cells Using a Protein Having an Ability to Recognize and Bind to a DNA Strand Break and an Antibody which Specifically Bind to the Protein This example shows that a protein having an ability to recognize and bind to a DNA strand break as prepared in Example 1 and a fluorescence labeled IgG antibody are used to detect a DNA strand break generated by gamma ray irradiation in mitochondria DNA of CHO-K1 cells.

CHO-K1 cells which were adhered on a cover glass were prepared by the same method as Example 2-(1). MitoRed (excitation wavelength at 560 nm; Dojin kagaku), which can specifically stain mitochondria, was applied to the cells at a final concentration of 100 nM, which were incubated in $CO_2$ incubator (5% $CO_2$) for 60 minutes at 37° C. After incubation, the cells were irradiated with 0, 5, 10, and 20 Gy of gamma ray which were generated from $^{60}Co$ as a radiation source using a similar method to that of Example 2-(2). Then, the cells were fixed just after the irradiation by a similar method to that of Example 2-(3). The fixed cells were washed twice with mild stirring in Buffer 1, as described in Example 2-(4), for 5 minutes at room temperature. After that, the cells were incubated with Buffer 1 containing 1% Nonidet P40 (Roche) for 90 minutes at 37° C. to permeabilize the plasma membrane. After incubation for 90 minutes, the cells were washed three times with mild stirring using Buffer 1 for 5 minutes at room temperature.

The cells were blocked by a method similar to that of Example 2-(5). Then, the PprA protein having an ability to recognize and bind to a DNA strand break as prepared in Example 1-(1) was diluted with Buffer 2 to make a solution containing 1 µg/ml of the PprA protein. The solution containing the PprA protein was added to the cells and the cells were incubated for 60 minutes at 37° C. After the incubation for 60 minutes, the cells were washed twice with mild stirring using Buffer 2 containing 0.5% Triton X-100 for 5 minutes at room temperature. After washing twice, a solution containing 3 µg/ml of a Cy2-labeled polyclonal anti-PprA IgG antibody in Buffer 2 as prepared in Example 1-(2) was added to the cells, which was incubated for 60 minutes at 37° C. under light shielding. Then, to remove any unbound antibody, the cells were washed twice with mild stirring using Buffer 2 containing 0.5% Triton X-100 for 5 minutes at room temperature.

Figure 5:
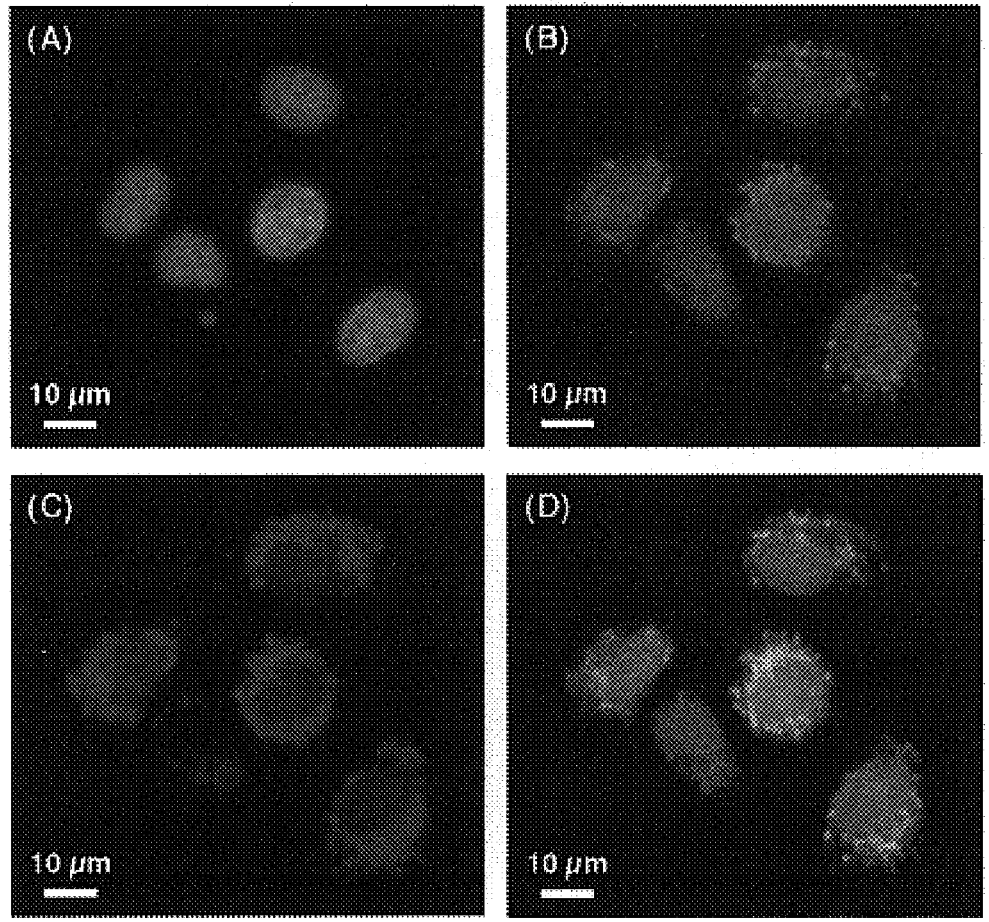
FIG. 5 consists of copies of photographs showing DNA strand breaks in mitochondria of CHO-K1 cells after gamma ray irradiation: (A) an image of nuclei detected by fluorescence of DAPI; (B) an image of DNA strand break(s) detected by fluorescence of Cy2; (C) an image of mitochondria detected by fluorescence of MitoRed; and (D) an image in which the fluorescence of DAPI (A), that of Cy2 (B) and that of MitoRed (C) are overlaid.
Figure 6:
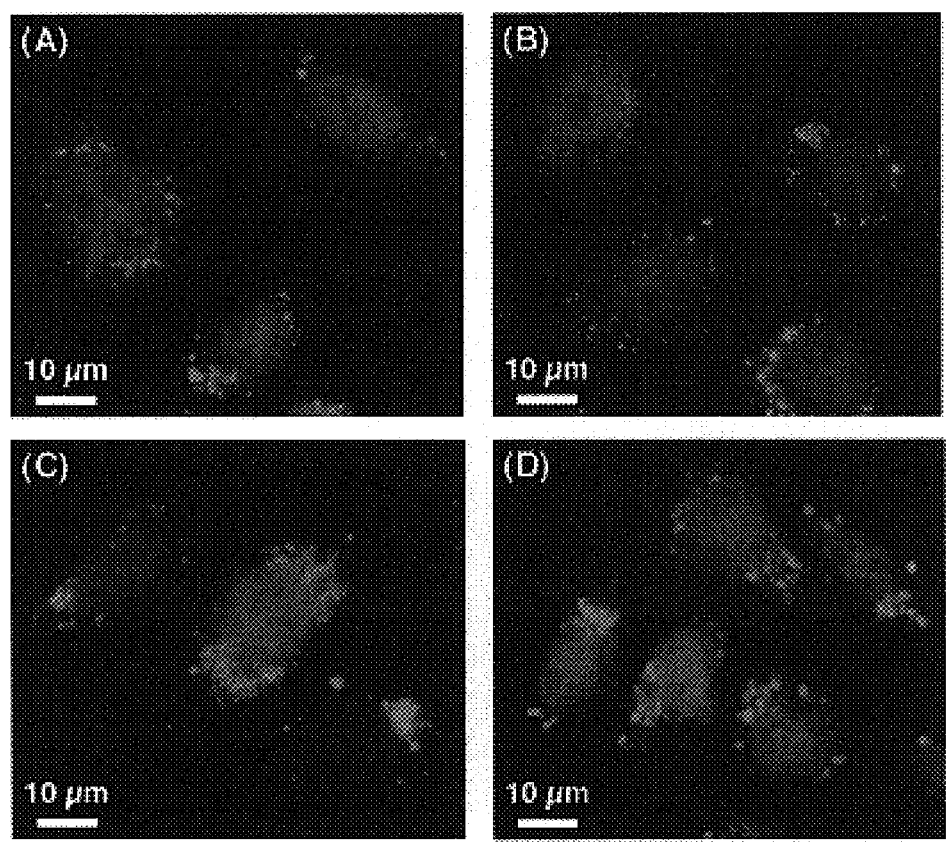
FIG. 6 consists of copies of photographs showing DNA strand breaks in mitochondria of CHO-K1 cells; (A) an image of DNA strand breaks detected by fluorescence of Cy2 in the cells which are not subjected to gamma ray irradiation; (B) an image of DNA strand breaks detected by fluorescence of Cy2 after 5 Gy of gamma ray irradiation; (C)

After staining the nuclei of the cells with DAPI by the similar method as Example 2-(7), the cells were mounted on a slide glass and were observed using a fluorescence microscope. The observation was carried out using a fluorescence microscope in which filters were appropriately set for fluorescence of DAPI, Cy2, or MitoRed. Photographs of fluorescence signals as produced were taken by a CCD camera. As a result, it was shown that fluorescence images of mitochondria visualized by MitoRed completely corresponded to that using Cy2 and that, therefore, the present method was determined to be able to effectively detect a DNA strand break existing in mitochondria (FIG. 5). Further, fluorescence intensities of Cy2 increased as dose of gamma ray increased, indicating that dose dependency of the number of DNA strand breaks in mitochondria on dose of gamma ray was also confirmed (FIG. 6).

INDUSTRIAL APPLICABILITY

The present invention provides a method for detecting an initial damage of DNA such as a DNA strand break which causes cell death or a mutation using the PprA protein derived from *Deinococcus radiodurans* or a fragment thereof and an antibody which specifically binds to the PprA protein or a fragment thereof. This detection method is useful for detecting initial damage to DNA which the individual cell under a culture condition or that of an animal tissue may suffer.

The present invention can be used to easily and effectively examine initial DNA damage of established cell line isolated from a living organism. Therefore, the present invention is particularly useful in the medical field, including a genotoxic test for detecting a substance which causes a DNA strand break. Since a genotoxic test has been designed to directly or indirectly detect a substance which causes genetic abnormality, a genotoxic test may be used to detect genetic alterations which are caused by various mechanisms in vitro and in vivo. For example, if a substance gives a positive result in a genotoxic test, such a result shows the possibility that the substance is carcinogenic. Thus, the result of a genotoxic test is expected to play an important role in the interpretation of carcinogenicity tests.

The present invention may also be useful for elucidating an effect of an antineoplastic antibiotic, such as bleomycin, which causes a DNA strand break in tumor cells. Further, the present invention may be useful for searching for a novel antineoplastic which causes a DNA strand break, such as bleomycin.

Further, the present invention is useful as a method for recognizing DNA damage caused by irradiation, and for easily detecting a radiation damage marker on DNA.

It is also possible to precisely detect dose dependency of the number of DNA breaks per dose of radiation by the present invention. Therefore, the present invention is expected to be useful as a biological dosimeter for measuring the extent of DNA strand break when the risk assessment is carried out regarding ionizing radiation, such as gamma ray or X ray, which triggers a DNA strand break.

What is claimed is:

1. A method for detecting in situ a DNA strand break, comprising:
   binding a PprA protein having an amino acid sequence of SEQ ID NO: 1, which is obtained from *Deinococcus radiodurans*, to a DNA strand break; and
   detecting in situ the PprA protein bound to the DNA strand break using an antibody or a fragment thereof which specifically binds to the PprA protein.

2. The method for detecting in situ a DNA strand break according to claim 1, wherein the antibody is a polyclonal antibody or a monoclonal antibody or the fragment thereof which is selected from the group consisting of Fab, F(ab')$_2$, and Fab'.

3. A kit for detecting in situ a DNA strand break, comprising:
   an amount of PprA protein having an amino acid sequence of SEQ ID NO: 1, which is obtained from *Deinococcus radiodurans*; and
   an antibody or a fragment thereof which specifically binds to the PprA protein.

4. The kit for detecting in situ a DNA strand break according to claim 3, wherein the antibody is a polyclonal antibody or a monoclonal antibody or the fragment thereof which is selected from the group consisting of Fab, F(ab')$_2$, and Fab'.

* * * * *